United States Patent [19]
Moretz et al.

[11] Patent Number: 5,435,014
[45] Date of Patent: Jul. 25, 1995

[54] GARMENT HAVING A SUSPENDED MOISTURE MANAGEMENT PANEL

[75] Inventors: Herbert L. Moretz, Davidson, N.C.; Daniel L. Brier, Key Largo, Fla.

[73] Assignee: Intelpro Corporation, Lincolnton, N.C.

[21] Appl. No.: 153,434

[22] Filed: Nov. 16, 1993

Related U.S. Application Data

[63] Continuation-in-part of Ser. No. 78,413, Jun. 17, 1993, which is a continuation-in-part of Ser. No. 47,841, Apr. 15, 1993, Pat. No. 5,392,467, which is a continuation-in-part of Ser. No. 23,006, Feb. 26, 1993, Pat. No. 5,249,320, which is a continuation-in-part of Ser. No. 3,263, Jan. 12, 1993, Pat. No. 5,269,720, which is a continuation-in-part of Ser. No. 991,761, Dec. 17, 1992, Pat. No. 5,297,296, which is a continuation-in-part of Ser. No. 945,677, Sep. 16, 1992, Pat. No. 5,291,617, which is a continuation-in-part of Ser. No. 842,224, Feb. 26, 1992, Pat. No. 5,210,882, which is a continuation-in-part of Ser. No. 791,066, Nov. 12, 1991, Pat. No. 5,217,782.

[51] Int. Cl.6 .................................................. A41B 9/02
[52] U.S. Cl. .................................... 2/403; 2/400; 2/402; 2/406; 604/393; 604/396
[58] Field of Search ............... 2/400, 402, 403, 406; 604/393, 396

[56] References Cited

U.S. PATENT DOCUMENTS

2,055,973  9/1936  Goss .
2,629,380  2/1953  Schweikert .
2,842,129  7/1958  Ernstorff .
3,043,307  7/1962  Weston .
3,237,625  3/1966  Johnson .
3,613,687  10/1971 Kennedy .
4,114,621  9/1978  Mims, Jr. .
4,215,685  8/1980  Ibel .
4,227,531  10/1980 McLeod .
4,280,230  7/1981  Lafleur ................................. 2/406
4,555,245  11/1985 Armbruster .
4,759,355  7/1988  Thrower .
4,870,958  10/1989 Webster .

Primary Examiner—Andrew M. Falik
Assistant Examiner—Gloria Hale
Attorney, Agent, or Firm—W. Thad Adams, III

[57] ABSTRACT

A garment having a moisture management suspended panel attached at one end thereof to a front waist area of the garment, and attached at a second end thereof to a back seat area of the garment. The suspended panel includes inner, intermediate, and outer fabric layers. The inner fabric layer is constructed of moisture wicking fibers for residing in skin contact during garment wear. The intermediate fabric layer resides adjacent to the inner fabric layer, and is formed of one or more fabrics for receiving and dispersing moisture wicked outwardly by the inner fabric layer. The intermediate fabric layer transports the moisture upwardly away from a lower crotch area of the garment and outwardly away from the skin of the wearer. The outer fabric layer includes a liquid impermeable, vapor permeable shield for providing a leak-proof barrier which prevents passage of liquid but permits dissipation of moisture in vapor form through the fabric. The shield resides adjacent to the intermediate fabric layer, and is the outermost fabric layer of the suspended panel.

20 Claims, 13 Drawing Sheets

GARMENT HAVING A SUSPENDED MOISTURE MANAGEMENT PANEL

TECHNICAL FIELD AND BACKGROUND OF THE INVENTION

This application is a continuation-in-part application of U.S. Ser. No. 078,413 filed Jun. 17, 1993, which is a continuation-in-part of U.S. Ser. No. 047,841 filed Apr. 15, 1993, now U.S. Pat. No. 5,392,467 which is a continuation-in-part of U.S. Ser. No. 023,006 filed Feb. 26, 1993, now U.S. Pat. No. 5,249,320 which is a continuation-in-part of U.S. Ser. No. 003,263 filed Jan. 12, 1993, now U.S. Pat. No. 5,269,720, which is a continuation-in-part of U.S. Ser. No. 991,761 filed Dec. 17, 1992, now U.S. Pat. No. 5,297,296, which is a continuation-in-part of U.S. Ser. No. 945,677 filed Sep. 16, 1992, now U.S. Pat. No. 5,291,617 which is a continuation-in-part of U.S. Ser. No. 842,224 filed Feb. 26, 1992, now U.S. Pat. No. 5,210,882, is a continuation-in-part of U.S. Ser. No. 791,066 filed Nov. 12, 1991 now U.S. Pat. No. 5,217,782.

The invention relates to a garment having a moisture management suspended panel incorporated therein for quickly wicking moisture away from the skin of the wearer, and moving the moisture upwardly to drier areas of the garment for evaporation. Garments incorporating the suspended panel are specifically intended to be indistinguishable in outward appearance from similar garments without such a panel.

Unlike many prior art moisture managing products, the garment having the moisture management suspended panel of the present invention does not absorb and hold moisture against the skin. Instead, the invention manages moisture by moving it outwardly away from the skin and upwardly towards the drier waist area of the suspended panel for evaporation. The suspended panel fits closely and comfortably against the skin, and thus, more effectively prevents leakage and spotting of moisture on the shell fabric of the garment, and on the outer clothing of the wearer.

The garment of the present invention can be worn over an extended period of time, and is specifically intended to receive and properly manage multiple instances of minor wetting without having to change the garment. This is virtually essential if the garment is going to be used by active wearers, particularly those in the business or work environment where storage and use of bulky diaper-like products is difficult if not impossible to accomplish without embarrassment. The availability of such a garment will permit the wearer to avoid use of bulky disposable garments, and will promote self-esteem.

Unlike many disposable urinary incontinence products, the present garment can be repeatedly laundered and worn. As a result, the garment it far less expensive than disposable products. Moreover, disposal products typically require frequent changing, and do not promote the evaporation of moisture.

SUMMARY OF THE INVENTION

Therefore, it is an object of the invention to provide a garment having a moisture management suspended panel.

It is another object of the invention to provide a garment having a moisture management suspended panel wherein the panel is constructed of a multi-layer composite material which quickly wicks moisture away from the skin, and moves the moisture upwardly towards drier areas of the garment and suspended panel for dispersal and evaporation. The suspended panel does not absorb moisture, and hold the moisture against the skin of the wearer.

It is another object of the invention to provide a garment having a moisture management suspended panel wherein the garment is a boxer-type undergarment or a pajama bottom for men or women.

It is another object of the invention to provide a garment having a suspended panel wherein the outermost layer of the suspended panel is a shield which permits dissipation of moisture in vapor form, but prevents the seepage of liquid moisture from the panel.

It is another object of the invention to provide a garment having a moisture management suspended panel wherein the suspended panel is attached at respective ends of the panel to the garment by elastic end segments which permit the panel to reside closely and comfortably next to the skin of the wearer.

It is another object of the invention to provide a garment having a moisture management suspended panel wherein the suspended panel includes an intermediate layer formed of one or more fabrics.

It is another object of the invention to provide a garment having a moisture management suspended panel wherein the panel can effectively manage between 1 and 2 ounces of liquid moisture at any given time.

It is another object of the invention to provide a garment having a moisture management suspended panel wherein the panel can effectively manage between 3 and 8 ounces of liquid moisture at any given time.

These and other objects of the present invention are achieved in the preferred embodiments disclosed below by providing a garment having a moisture management suspended panel attached at one end thereof to a front waist area of the garment, and attached at a second end thereof to a back seat area of the garment. The suspended panel includes inner, intermediate, and outer fabric layers. The inner fabric layer is constructed of moisture wicking fibers for residing in skin contact during garment wear. The intermediate fabric layer resides adjacent to the inner fabric layer, and is formed of one or more fabrics for receiving and dispersing moisture wicked outwardly by the inner fabric layer. The intermediate fabric layer transports the moisture upwardly away from a lower crotch area of the garment and outwardly away from the skin of the wearer. The outer fabric layer includes a liquid impermeable, vapor permeable shield for providing a leak-proof barrier which prevents passage of liquid but permits dissipation of moisture in vapor form through the fabric. The shield resides adjacent to the intermediate fabric layer, and is the outermost fabric layer of the suspended panel.

According to one preferred embodiment of the invention, the intermediate fabric layer of the suspended panel is a moisture transport insert having a lower first portion and an upper second portion. The lower first portion resides generally adjacent a lower crotch area of the garment and is relatively narrow with a relatively small surface area. The upper second portion of the moisture transport insert resides generally adjacent an upper crotch area of the garment, and is relatively wide with a relatively large surface area. The second portion provides greater moisture absorption capacity in the upper crotch area to promote the transport of moisture upwardly towards a drier area of the suspended panel where moisture can be more easily dispersed.

Preferably, the width of the moisture transport insert tapers from the relatively wide second portion towards the relatively narrow first portion.

According to another preferred embodiment of the invention, the intermediate fabric layer of the suspended panel includes a first and second fabric. The first fabric is a moisture wicking overlay carried by the suspended panel for moving moisture away from the skin. The moisture wicking overlay has a skin-side surface and a shell-side surface, and the overlay defines an opening therethrough from the skin-side surface to the shell-side surface.

The second fabric is a moisture transport insert extending through the opening in the moisture wicking overlay. The insert has a lower first portion and an upper second portion. The lower first portion is positioned in overlying relation on the skin-side surface of the moisture wicking overlay for receiving moisture from the skin and from the moisture wicking overlay. The upper second portion is positioned in overlying relation on the shell-side surface of the moisture wicking overlay for receiving moisture from the first portion of the moisture transport insert and for transporting the moisture through the opening to the shell-side surface of the moisture wicking overlay for dispersal.

According to another preferred embodiment of the invention, the moisture wicking overlay defines a second opening therethrough located in spaced-apart relation to the first opening for inserting a free end of the first portion of the moisture transport insert through the moisture wicking overlay from the skin-side surface of the moisture wicking overlay to the shell-side surface of the moisture wicking overlay.

According to yet another preferred embodiment of the invention, the moisture wicking overlay is a fabric constructed substantially of moisture wicking fibers having a high surface area in relation to volume.

According to yet another preferred embodiment of the invention, the moisture wicking overlay is an integrally knit bi-component fabric constructed of moisture wicking fibers on the skin-side surface thereof for residing nearest the skin of the wearer, and hydrophilic fibers on the shell-side surface thereof for residing away from the skin of the wearer.

According to yet another preferred embodiment of the invention, the moisture transport insert is attached to the moisture wicking overlay by sew stitching a portion of the moisture transport insert to the moisture wicking overlay.

According to yet another preferred embodiment of the invention, the moisture transport insert comprises a fabric constructed substantially of moisture wicking fibers having a high surface area in relation to volume.

Preferably, the moisture transport insert comprises hydrophilic nylon fibers chemically processed for speeding the movement of moisture along the shaft of the fibers.

According to another preferred embodiment of the invention, the moisture transport insert comprises an integrally knit bi-component fabric constructed of moisture wicking fibers on the skin-side surface thereof for residing nearest the skin of the wearer, and hydrophilic fibers on the shell-side surface thereof for residing away from the skin of the wearer.

Preferably, the moisture wicking fibers of the bi-component moisture transport insert are hydrophilic nylon fibers.

Preferably, the hydrophilic fibers of the bi-component moisture transport insert comprise cotton fibers for absorbing and dispersing moisture wicked outwardly by the moisture wicking fibers.

According to another preferred embodiment of the invention, the inner fabric layer is constructed substantially of moisture wicking fibers having a high surface area in relation to volume.

According to yet another preferred embodiment of the invention, the inner fabric layer is an integrally knit bi-component fabric constructed of moisture wicking fibers on a skin-side surface thereof for residing nearest the skin of the wearer, and hydrophilic fibers on an shell-side surface thereof for residing away from the skin of the wearer.

Preferably, the moisture wicking fibers of the bi-component inner fabric layer are hydrophobic polyester fibers.

Preferably, the hydrophilic fibers of the bi-component inner fabric layer are hydrophilic nylon fibers.

According to another preferred embodiment of the invention, the inner fabric layer is an integrally knit tri-component fabric constructed of hydrophobic moisture wicking fibers on a skin-side surface thereof for residing nearest the skin of the wearer, a first hydrophilic fiber component residing adjacent to the moisture wicking fibers, and a second hydrophilic fiber component residing adjacent to the first hydrophilic fiber component and comprising the shell-side surface of the tri-component fabric.

Preferably, the surface of the second hydrophilic fiber component adjacent to the first hydrophilic fiber component is brushed for enhancing the ability of the second hydrophilic component to disperse moisture moved outwardly from the first hydrophilic component.

According to another preferred embodiment of the invention, the suspended panel is attached at respective ends thereof to the garment by first and second elastic end segments. Each of the end segments is constructed of elastic yarns to provide stretchability for allowing the suspended panel to reside closely and comfortably next to the skin of the wearer.

BRIEF DESCRIPTION OF THE DRAWINGS

Some of the objects of the invention have been set forth above. Other objects and advantages of the invention will appear as the invention proceeds when taken in conjunction with the following drawings, in which.

DESCRIPTION OF THE PREFERRED EMBODIMENT AND BEST MODE

Figure 1:
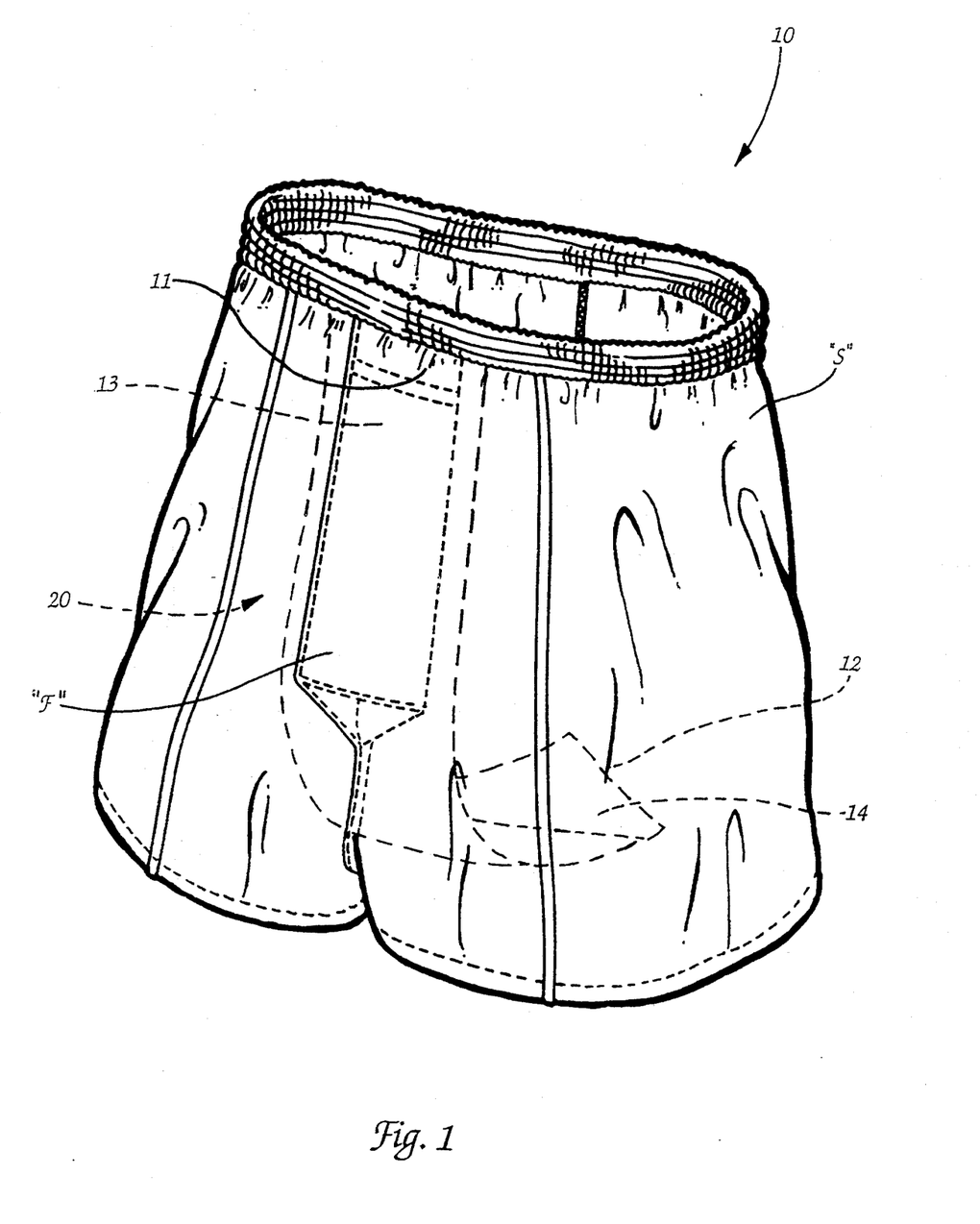
FIG. 1 is a perspective view of the invention according to one preferred embodiment showing the moisture management suspended panel in phantom.

Referring now specifically to the drawings, a garment according to the present invention is illustrated in FIG. 1 and shown generally at reference numeral 10. The garment 10 includes a moisture management suspended panel 20 attached at a first end thereof to the front waist area 11 of the garment 10, and attached at a second end thereof to the back seat area 12 of the garment 10. Except for the suspended panel 20, the garment 10 is constructed in a conventional manner to resemble a conventional garment in outward appearance. In addition, the garment 10 is launderable and reusable.

Preferably, the suspended panel 20 is attached at respective ends thereof to the garment 10 by first and second elastic end segments 13 and 14 which are sewn to the garment 10, and attached, respectively, to the suspended panel 20 by conventional sew techniques known in the art. The end segments 13, 14 are constructed of elastic yarns, such as spandex or "Lycra" to provide stretchability for allowing the suspended panel 20 to reside closely and comfortably next to the skin of the wearer.

Figure 2:
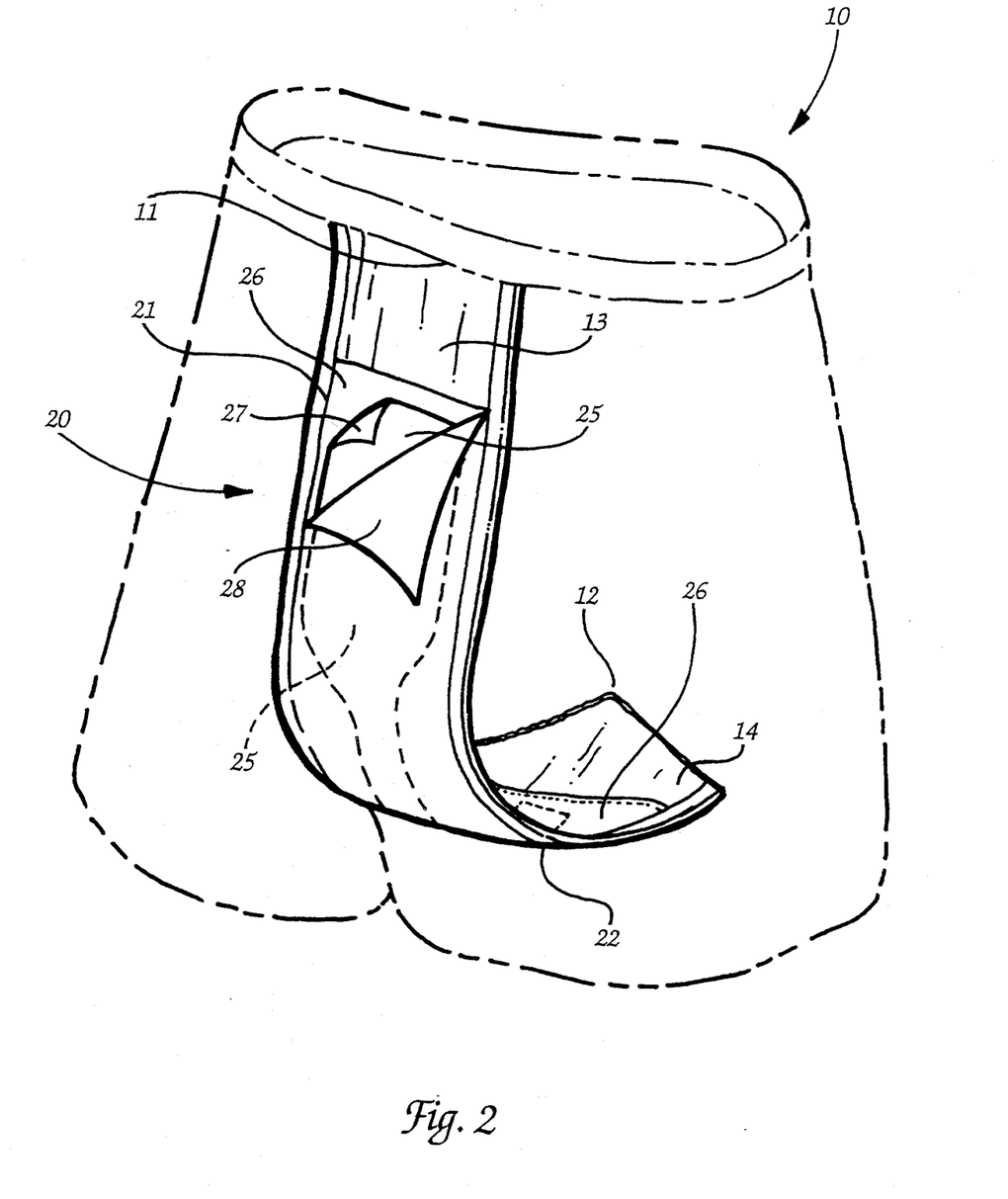
FIG. 2 is a perspective view of the moisture management suspended panel showing the garment in phantom.

As best shown in FIG. 2, the suspended panel 20 of the garment 10 includes a plurality of fabric layers; an inner fabric layer 26 for residing in skin contact during garment wear, an intermediate fabric layer 27 residing adjacent to the inner fabric layer 26, and an outer fabric layer 28 forming the outermost fabric layer of the suspended panel 20. The fabric layers 26, 27, and 28 of the suspended panel 20 are preferably attached together by sewing the perimeter edges of the respective layers 26–28 to adjacent layers to form a composite, multi-layered fabric panel.

Each of the fabric layers 26–28 has a skin-side surface and a shell-side surface. These terms indicate the side of the fabric layer closer to the skin during garment wear, and the side closer to the shell fabric "S" (See FIG. 1) of the garment 10, respectively. The terms are not intended to infer that the skin-side surface of the particular fabric layer is in direct contact with the skin, or that the shell-side surface is in direct contact with the shell fabric "S" of the garment 10.

Figure 3:
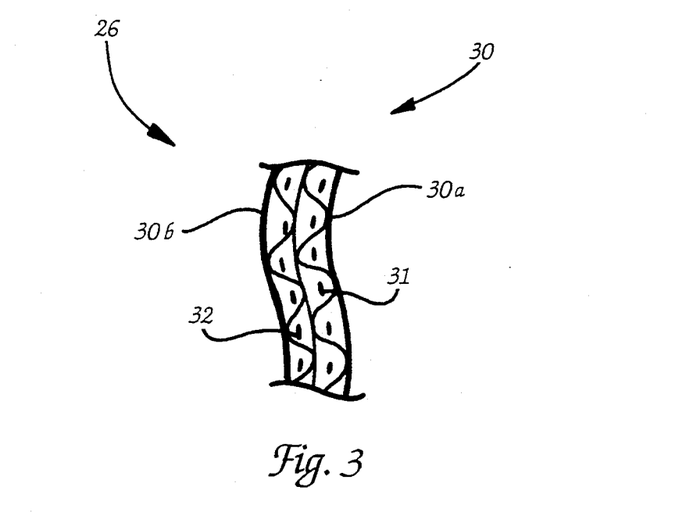
FIG. 3 is an exaggerated cross-sectional view of the bi-component fabric of the inner fabric layer of the suspended panel according to one preferred embodiment.

As shown in FIG. 3, the inner fabric layer 26 is preferably constructed of an integrally-knit bi-component fabric 30 having moisture wicking fibers 31 on a skin-side surface 30a, and hydrophilic fibers 32 on a shell-side surface 30b away from the skin. The moisture wicking fibers 31 of the skin-side surface 30a are preferably hydrophobic polyester fibers which quickly move moisture away from the skin and towards the outer layers of the suspended panel 20. The "Coolmax" polyester fibers manufactured by Dupont Corporation are preferably chosen for their exceptional ability to wick and move moisture.

The hydrophilic fibers 32 of the bi-component fabric 30 on the shell-side surface 30b may be cotton, hydrophilic nylon, rayon, wool, blends of these fibers, or other similar hydrophilic fibers. Preferably, the hydrophilic fibers 32 are hydrophilic nylon, such as the "Hydrofil" fibers manufactured by Allied Fibers Corporation.

Figure 4:
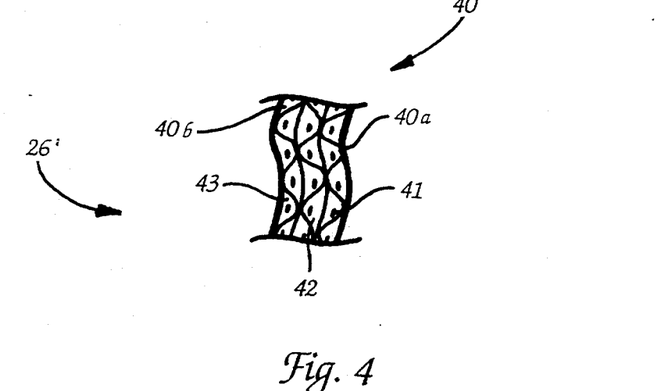
FIG. 4 is an exaggerated cross-sectional view of the tri-component fabric of the inner fabric layer of the suspended panel according to another preferred embodiment.

In a second embodiment, the inner fabric layer 26' is constructed of a tri-component fabric 40. As shown in FIG. 4, a second integrally-knit hydrophilic nylon component 43 resides adjacent to a first hydrophilic component 42, identical to the hydrophilic component of the bi-component fabric 30 described above. Wicking fibers 41, identical to those described above with reference to the bi-component fabric 30, reside nearest the skin, and comprise the skin-side surface 40a of the tri-component fabric 40. Preferably, the second hydrophilic component 43 is hydrophilic nylon which has a brushed outer surface. The brushed surface resides next to the first hydrophilic component 42 to enhance the ability of the fabric 40 to disperse moisture moved outwardly away from the body. The hydrophilic fabric may be the "Hydrofil" fibers manufactured by Allied Fibers Corporation, or "Intera" nylon as manufactured and treated by the Intera Corporation.

In a third embodiment (not shown), the inner fabric layer is constructed of a single knit fabric formed substantially of hydrophobic polyester or polypropylene fibers. These fibers have a relatively high surface area in relation to volume.

Figure 5:
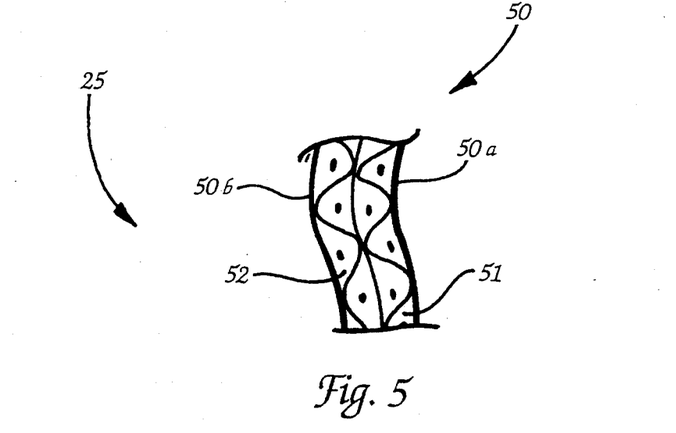
FIG. 5 is an exaggerated cross-sectional view of the bi-component fabric of the moisture transport insert of the suspended panel according to one preferred embodiment.

As best shown in FIG. 2, the intermediate fabric layer 27 of the suspended panel 20 is a moisture transport insert 25 which resides adjacent to the shell-side surface of the inner fabric layer 26. As shown in FIG. 5, the moisture transport insert 25 is preferably constructed of an integrally knit bi-component fabric 50 formed of moisture wicking fibers 51 and moisture absorbing fibers 52. The moisture wicking fibers 51 are located substantially on the skin-side surface 50a of the bi-component fabric 50, and act to move moisture outwardly along the longitudinal shafts of the fibers. These fibers are preferably hydrophilic nylon fibers such as "Hydrofil," but may include other hydrophobic fibers such as polypropylene or "Coolmax" polyester.

The integrally-formed, moisture absorbing fibers 52 are located next to the moisture wicking fibers 51 on the shell-side surface 50b of the bi-component fabric 50. The moisture absorbing fibers 52 act to absorb and disperse moisture wicked outwardly by the moisture wicking fibers 51. The moisture absorbing fibers 52 may include cotton, rayon, wool, blends of these fibers, or other similar hydrophilic fibers.

The effect of body heat and the integral combination of moisture wicking fibers and moisture absorbing fibers, as described above, produces a capillary action. Moisture is drawn from the inner fabric layer 26 of the suspended panel 20, and pulled outwardly away from the body and upwardly towards the waist area 11 of the garment 10 and suspended panel 20. In the upper area of the suspended panel 20, the moisture is more readily dispersed and evaporated.

In another embodiment (not shown), the moisture transport insert 25 is formed of a single knit moisture wicking fabric layer. Preferably, the single layer is constructed of hydrophilic nylon fibers, or "Intera" treated fibers which act to quickly wick and move moisture away from the body. Alternatively, the single layer may be constructed of polyester fibers, such as the "Coolmax" fabric manufactured by DuPont, or the "Polartec" fabric manufactured by Malden Mills, Inc.

Figure 6:
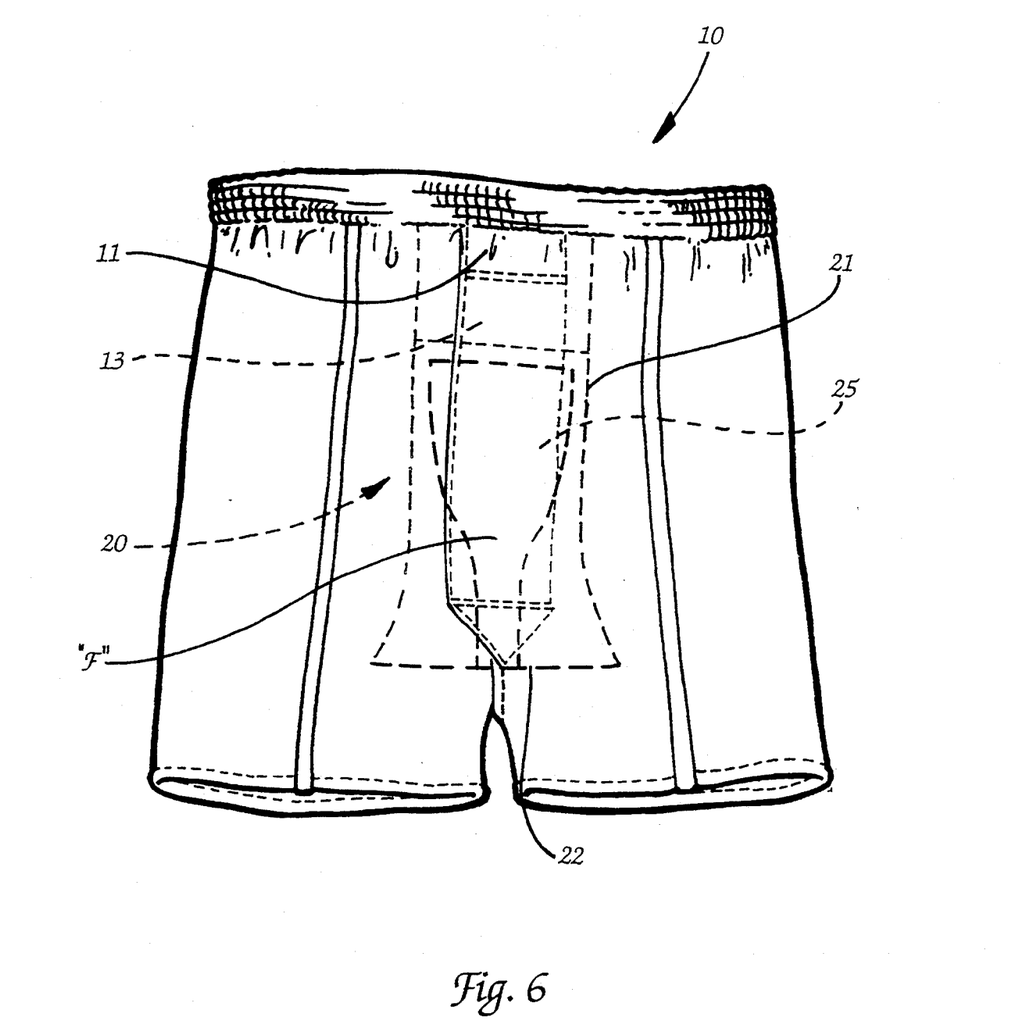
FIG. 6 is a front elevational view of the garment showing the suspended panel in phantom.
Figure 7:
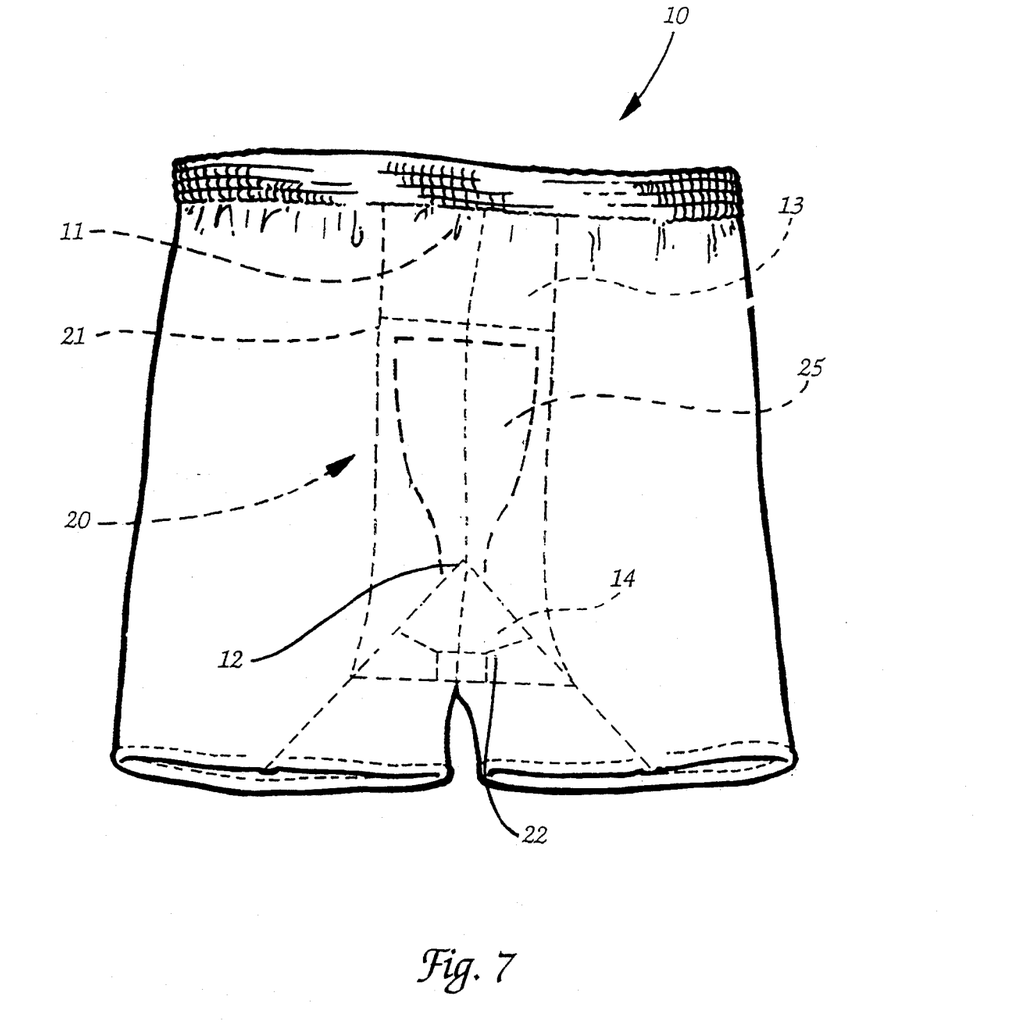
FIG. 7 is a back elevational view of the garment showing the suspended panel in phantom.
Figure 8:
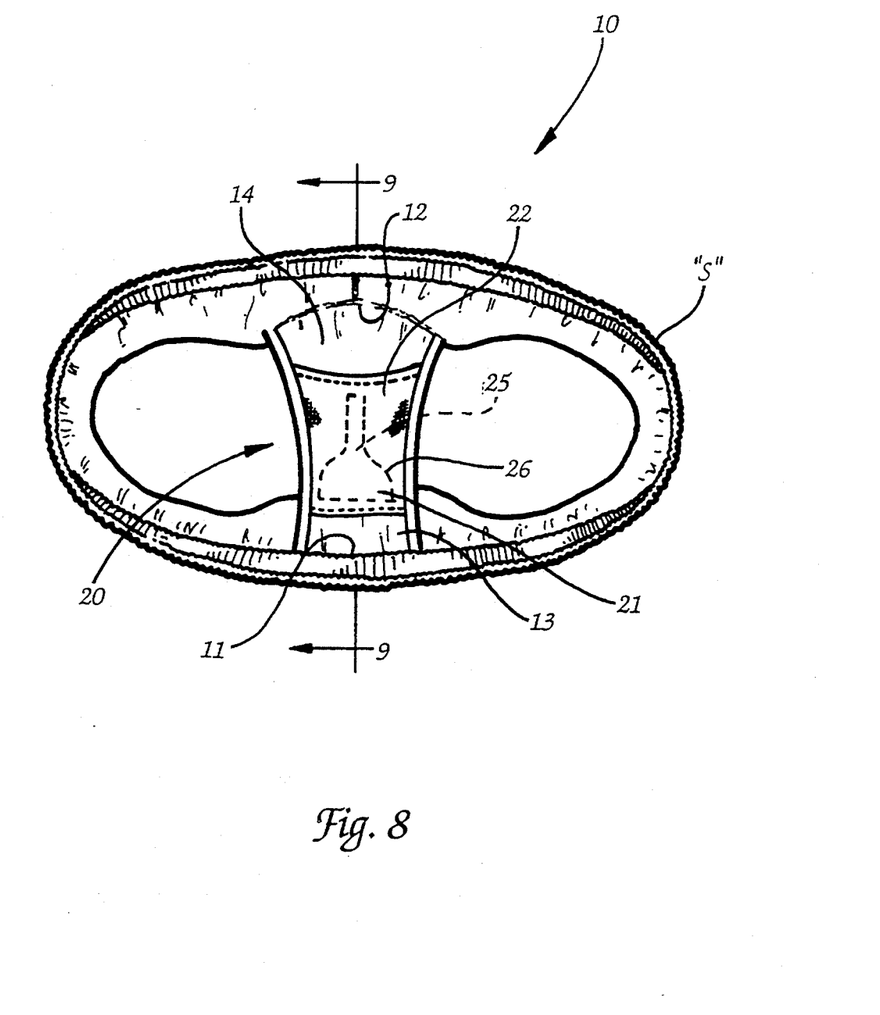
FIG. 8 is a top plan view of the garment and suspended panel according to a preferred embodiment.
Figure 9:
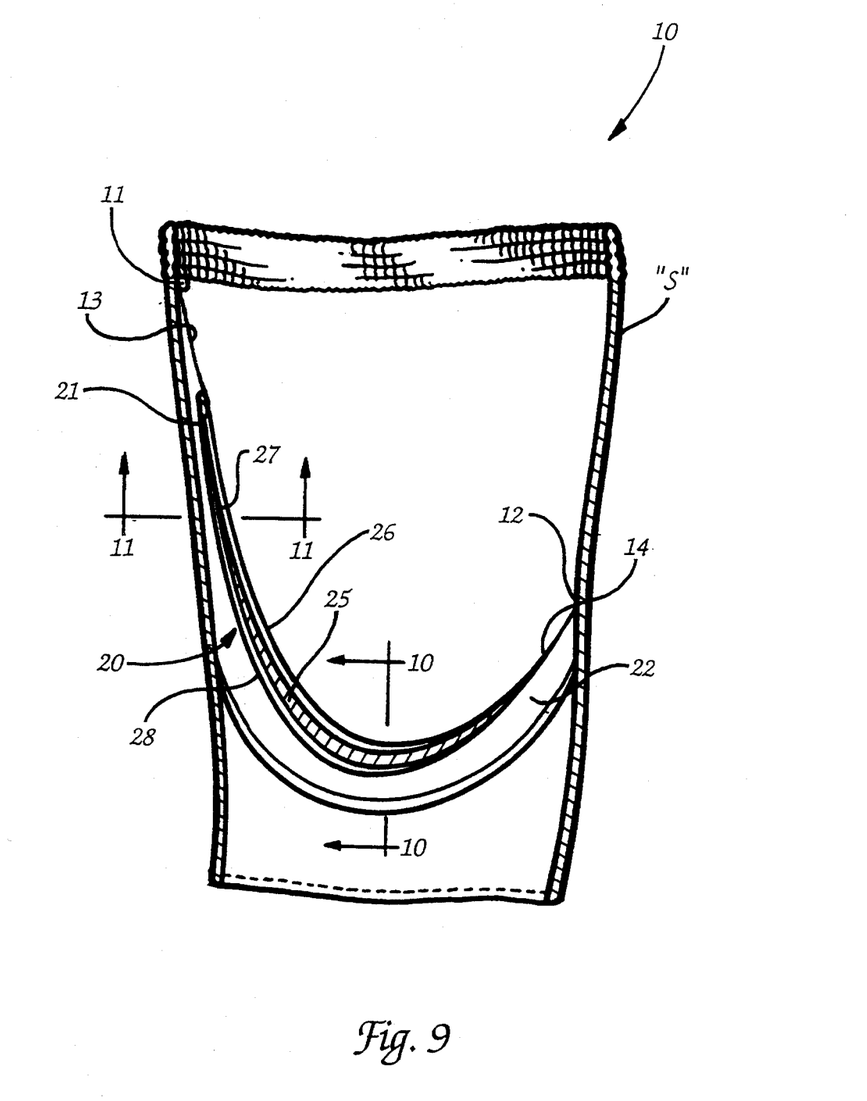
FIG. 9 is a cross-sectional side view of the garment and suspended panel taken substantially along lines 9—9 of FIG. 8.
Figure 10:
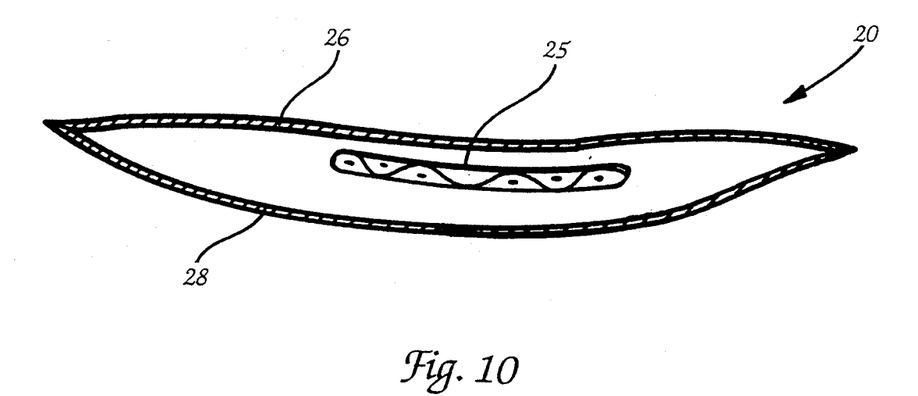
FIG. 10 is a cross-sectional view of the suspended panel taken substantially along lines 10—10 of FIG. 9.
Figure 11:
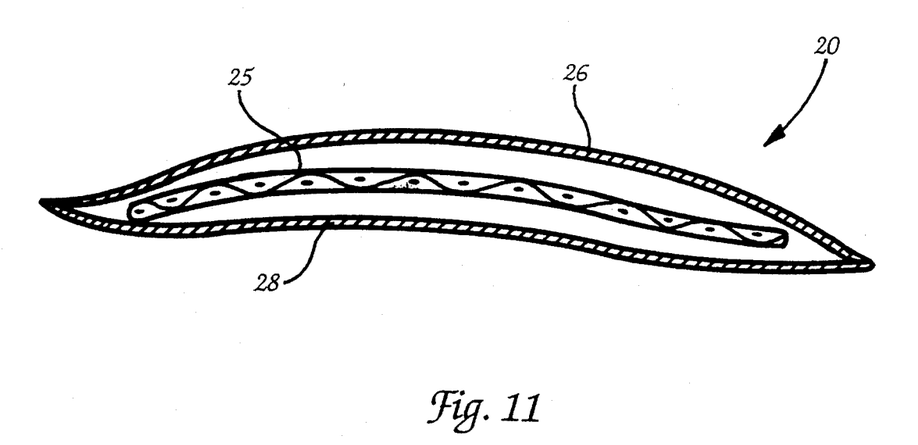
FIG. 11 is a cross-sectional view of the suspended panel taken substantially along lines 11—11 of FIG. 9.

As best shown in FIGS. 6, 7, and 8, the moisture transport insert 25 is shaped to taper from top to bottom, or from an upper crotch area 21 of the garment 10 to a lower crotch area 22 of the garment 10. The upper crotch area 21 of the garment 10 is defined as extending generally from just beneath the front waist area 11 of the garment 10 downwardly to the bottom end of the fly opening "F." The lower crotch area 22 is defined as extending from the bottom end of the fly opening "F" to just below the seat area 12 of the garment 10. The tapering effect of the moisture transport insert 25 provides greater moisture absorption and dispersal capacity in the upper portion of the suspended panel 20, where moisture can be carried to drier areas for quicker evaporation. Moreover, the relatively narrow strip of moisture transport insert 25 positioned in the lower crotch area 22 provides less bulk between the legs and greater comfort to the wearer. FIGS. 9, 10, and 11 illustrate a cross-sectional view of the garment 10 and suspended panel 20, and the relative width and position of the moisture transport insert 25 as contained in the suspended panel 20. According to another embodiment (not shown), the moisture transport insert is triangular, or rectangular.

Referring again to FIG. 2, the outer fabric layer 28 of the suspended panel 20 is constructed of a liquid impermeable, vapor permeable shield. The shield resides adjacent to the shell-side surface of the moisture transport insert 25, and is preferably constructed of woven nylon or polyester microfibers. Although the shield is liquid impervious, it permits the dissipation of moisture from the suspended panel 20 in vapor form. In one embodiment, particularly for individuals with mild incontinence, the shield will permit the suspended panel 20 to effectively manage approximately 1-2 ounces of moisture without any staining or seepage of moisture to the outer shell "S" of the garment 10.

In another embodiment, the shield may be constructed of woven nylon or polyester microfibers with a thin teflon coating on the skin-side surface of the shield to block relatively large amounts of moisture, even under the body pressure of the wearer. An example of such a fabric shield is that manufactured by the W. L. Gore Company and sold under the trademark "Gore-tex." The use of a "Gore-tex" shield in the garment 10 will permit the suspended panel 20 to effectively manage approximately 4-6 ounces of moisture at a time.

Since the shield does not produce a rustling or crinkling noise when worn, it is particularly desirably for use in the garment 10. The conventional appearance and feel of the garment 10 helps avoid any embarrassment to the wearer because of the need or desire to wear moisture management garments.

Figure 12:
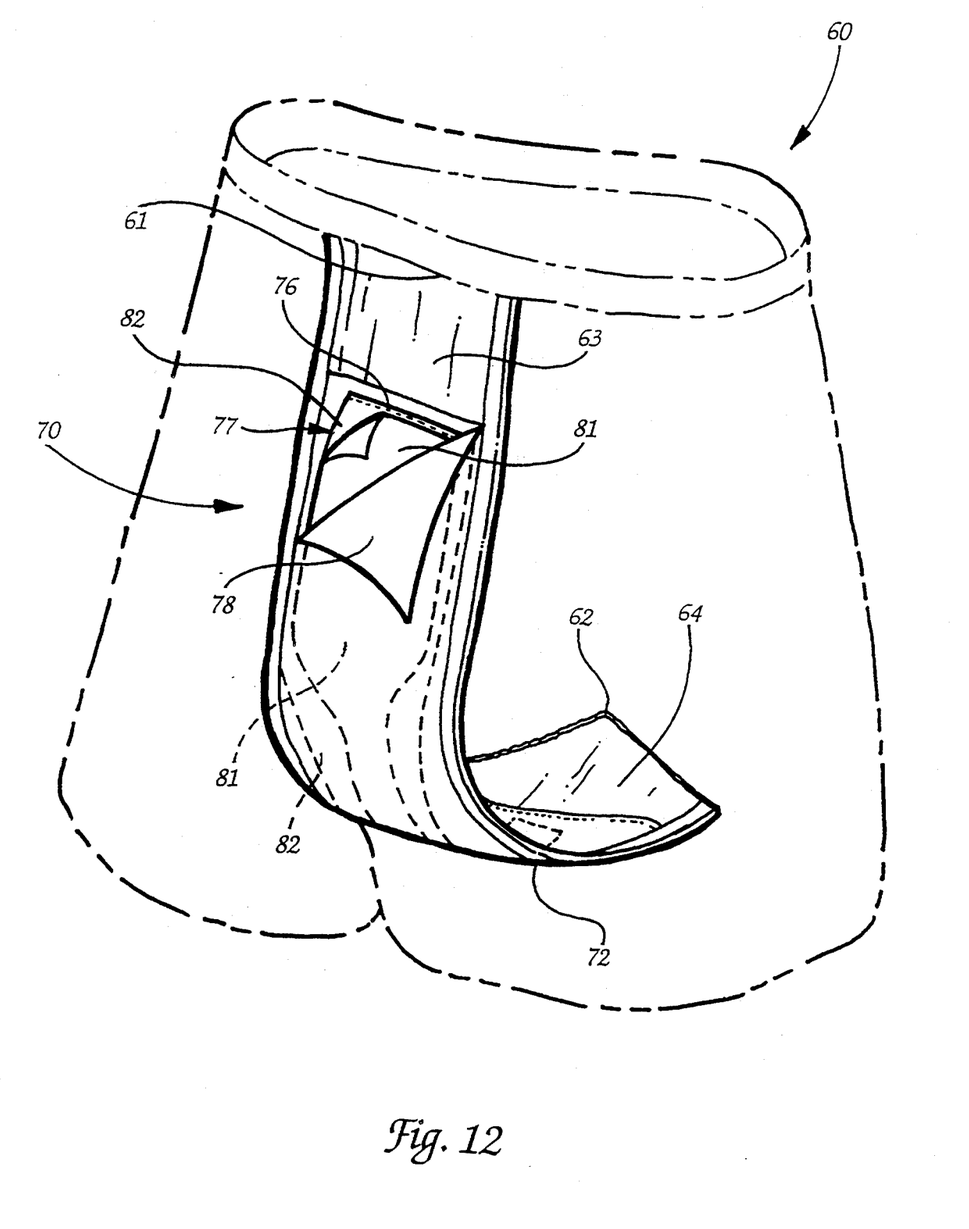
FIG. 12 is a perspective view of the moisture management suspended panel according to another preferred embodiment showing the garment in phantom.

Referring now to FIG. 12, another embodiment of the garment 60 and moisture management suspended panel 70 is illustrated. The suspended panel 70 is attached at a first end thereof to the front waist area 61 of the garment 60, and attached at a second end thereof to the back seat area 62 of the garment 60. Preferably, the suspended panel 70 is attached at respective ends to the garment 60 by first and second elastic end segments 63 and 64 which are sewn to the garment 60, and attached, respectively, to the suspended panel 70 by conventional sew techniques known in the art. The end segments 63, 64 are constructed of elastic yarns, such as spandex or "Lycra", to provide stretchability for allowing the suspended panel 70 to reside closely and comfortably next to the skin of the wearer.

As shown in FIG. 12, the suspended panel 70 includes an inner fabric layer 76 for residing in skin contact during garment wear, an intermediate fabric layer 77 residing adjacent to the inner fabric layer 76, and an outer fabric layer 78 forming the outermost fabric layer of the suspended panel 70. The fabric construction, orientation, and various embodiments of the inner and outer fabric layers 76 and 78 of the suspended panel 70 are identical to that described above with reference to the inner and outer fabric layers 26 and 28 of the suspended panel 20 illustrated in FIGS. 1–11.

Figure 13:
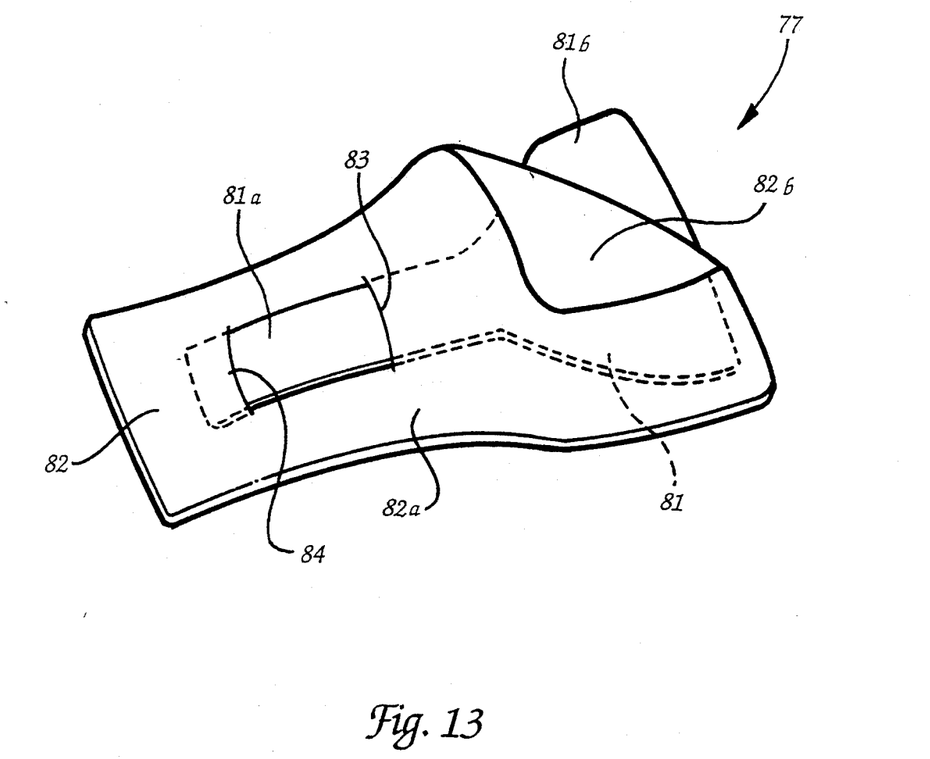
FIG. 13 is a perspective view of the intermediate fabric layer of the suspended panel illustrated in FIG. 12, showing particularly the moisture transport insert and the moisture wicking overlay.

As best shown in FIG. 13, the intermediate fabric layer 77 of the suspended panel 70 includes both a moisture transport insert 81 and a moisture wicking overlay 82. The moisture transport insert 81 and moisture wicking overlay 82 are preferably attached together to function as a unit by sewing a top and bottom section of the moisture transport insert 81 to the moisture wicking overlay 82. The moisture transport insert 81 and moisture wicking overlay 82 are described in detail below.

As shown in FIG. 13, the moisture wicking overlay 82 has a first opening 83 formed therein through which the moisture transport 81 insert extends. The opening 83 defines first and second portions, 81a and 81b, of the moisture transport insert 81 extending in respective opposite directions from the opening 83, and along opposite surfaces of the moisture wicking overlay 82.

The first lower portion 81a of the moisture transport insert 81 resides on a skin-side surface 82a of the moisture wicking overlay 82 in overlying relation with the moisture wicking overlay 82. The first portion 81a has a relatively small and narrow surface area, and is preferably located in a lower portion of the suspended panel 70 generally corresponding to the lower crotch area 72 (See FIG. 12) of the garment 60. The narrow construction of the first portion 81a provides a more comfortable feel to the wearer in the lower crotch area 72 of the garment 60 with a minimal amount of wetness maintained in the lower crotch area 72 at any given time.

Figure 14:
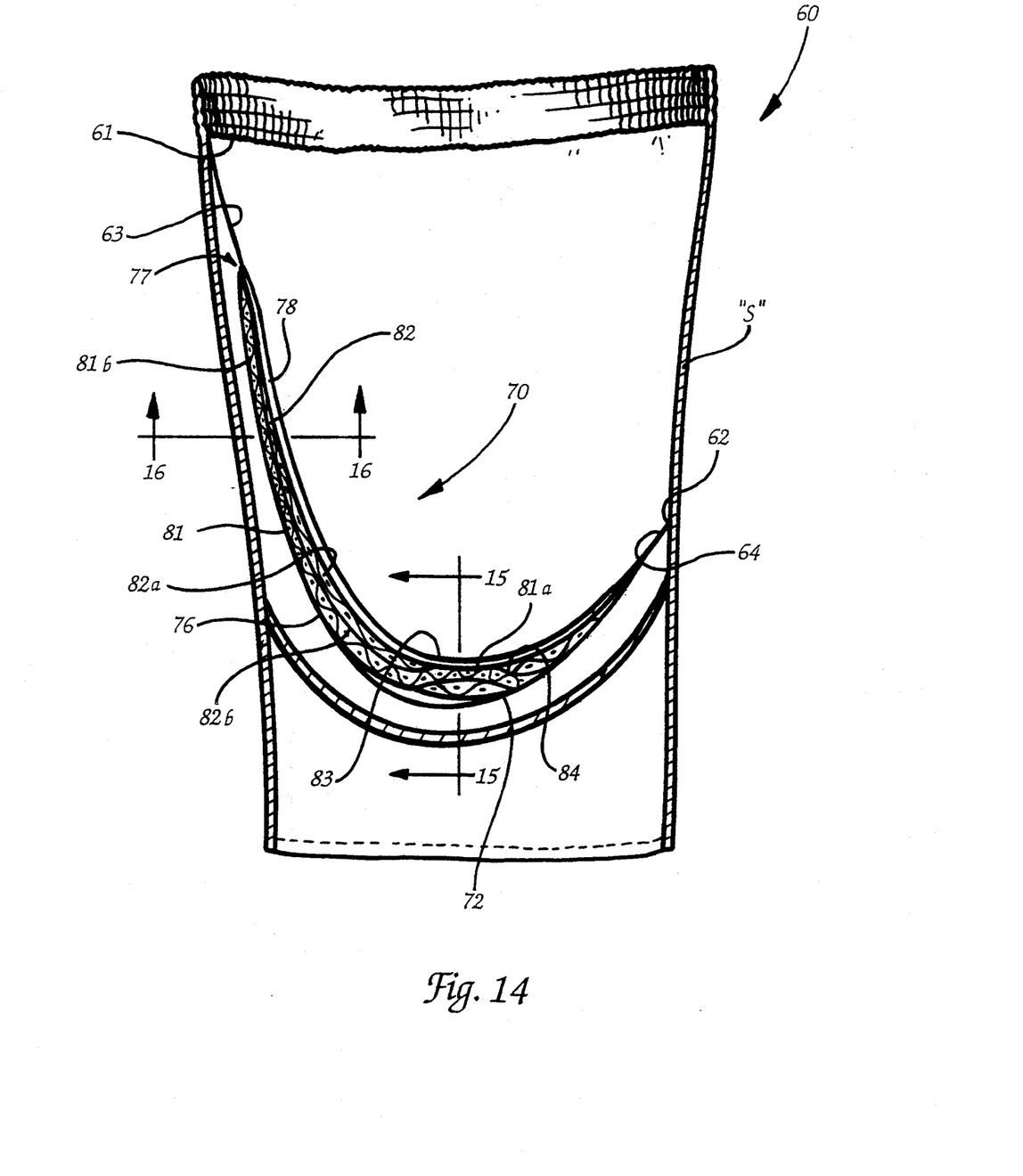
FIG. 14 is a cross-sectional side view of the garment and suspended panel according to the embodiment of the suspended panel illustrated in FIG. 12.
Figure 15:
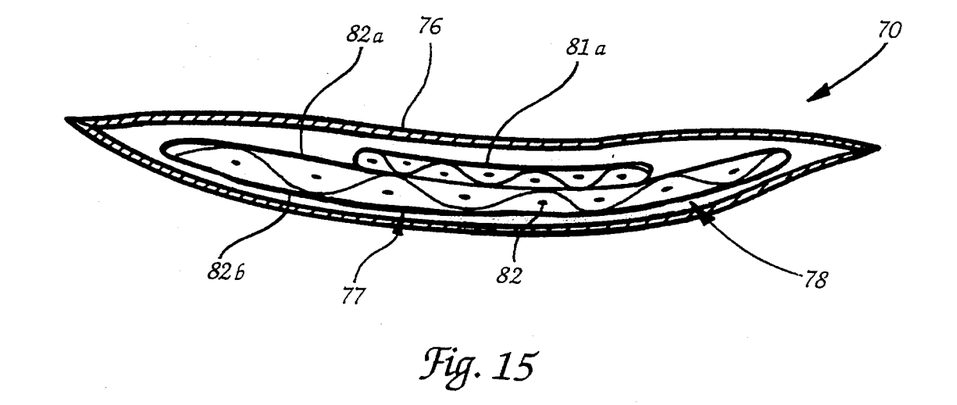
FIG. 15 is a cross-sectional view of the suspended panel taken substantially along lines 15—15 of FIG. 14.
Figure 16:
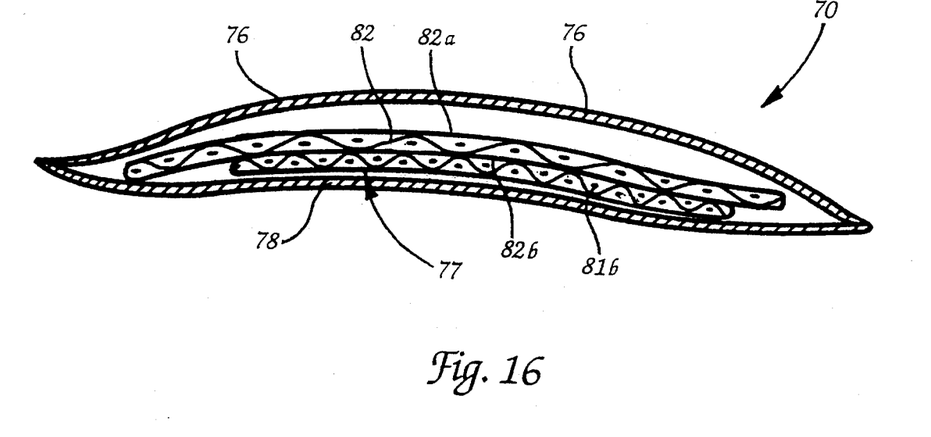
FIG. 16 is a cross-sectional view of the suspended panel taken substantially along lines 16—16 of FIG. 14.

The second, upper portion 81b of the moisture transport insert 81 resides on the shell-side surface 82b of the moisture wicking overlay 82 away from the skin, and has a relatively large surface area. Preferably, the second portion 82b tapers outwardly, gradually increasing in width from the opening 83, and extending upwardly substantially to the top of the moisture wicking overlay 82. FIGS. 15 and 16, illustrate respective cross-sections of the moisture wicking overlay 82 and moisture transport insert 81 taken substantially along lines 15–15 and 16–16 of FIG. 14 to show the orientation of these components with respect to the skin of the wearer.

The smaller surface area of the first portion 81a of the moisture transport insert 81 acts to receive moisture wicked outwardly from the skin by the inner fabric layer 76, and to quickly transport the moisture to the shell-side surface 82b of the moisture wicking overlay 82 away from the skin and along the fibers of the larger second portion 81b of the moisture transport insert 81. In the larger second portion 81b, moisture is more readily dispersed and moved outwardly and upwardly towards the drier waist area 61 of the garment 60. The position within the suspended panel 70 and garment 60 of the first and second portions 81a, b of the moisture transport insert 81 and the moisture wicking overlay 82 is best shown in FIGS. 14–16.

The moisture wicking overlay 82 may have a second opening 84 located beneath the first opening 83 for receiving the free end of the first portion 81a of the moisture transport insert 81, as shown in FIG. 13.

The moisture wicking overlay 82 and moisture transport insert 81 of the suspended panel 70 act to transport moisture upwardly away from the lower crotch area 72 and outwardly away from the skin of the wearer by the movement of moisture along the longitudinal shafts of the fibers. The fiber composition of the moisture wicking overlay 82 and moisture transport insert 81 is described below with reference to FIGS. 17 and 18.

Figure 17:
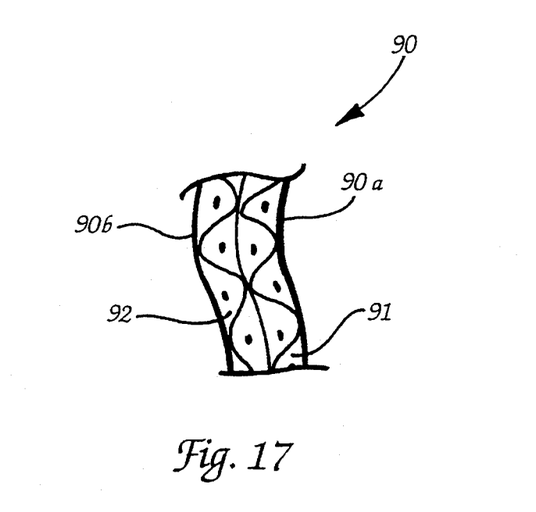
FIG. 17 is an exaggerated cross-sectional view of the bi-component fabric of the moisture wicking overlay of the suspended panel according to the embodiment illustrated in FIG. 12.

Preferably, the moisture wicking overlay 82 is an integrally knit bi-component fabric. As shown in FIG. 17, the bi-component fabric 90 includes moisture wicking fibers 91 located on a skin-side surface 90a, and hydrophilic fibers 92 located on a shell-side surface 90b. The skin-side surface 90a is preferably brushed to enhance the fabric's ability to receive and move moisture. The moisture wicking fibers 91 of the skin-side surface 90a are preferably polyester fibers. Alternatively, the moisture wicking fibers 91 may be "Intera" nylon fibers processed by the Intera Corporation. These "Intera" fibers are chemically treated to enhance the fibers' ability to quickly transport moisture. The hydrophilic fibers 92 may include cotton, hydrophilic nylon, rayon, wool, blends of these fibers, or other similar hydrophilic fibers. Alternately, the moisture wicking overlay 82 may be constructed of a single-layer fabric formed of "Intera" nylon fibers, polypropylene, or "Coolmax" polyester fibers. The "Coolmax" fibers have a relatively high surface area in relation to volume, with channels running longitudinally along the shaft of the fiber to enhance the wicking or transport of moisture. Such fibers are designed specifically to move or wick moisture.

Figure 18:
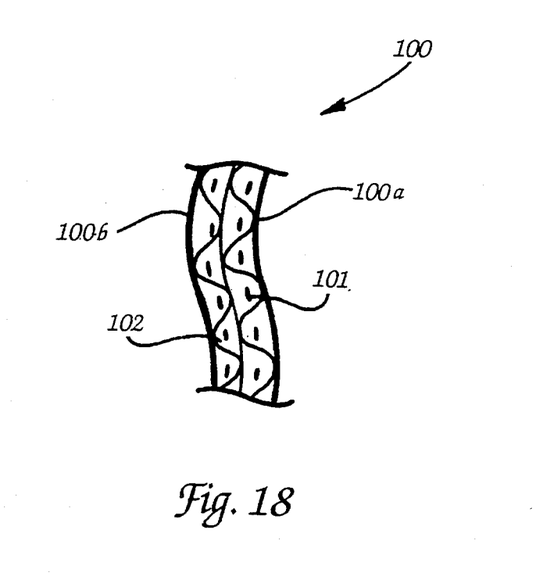
FIG. 18 is an exaggerated cross-sectional view of the bi-component fabric of the moisture transport insert of the suspended panel according to the embodiment illustrated in FIG. 12.

As shown in FIG. 18, the moisture transport insert 81 is preferably constructed of an integrally knit bi-component fabric 100 formed of moisture wicking fibers 101 on a skin-side surface 100a, and hydrophilic fibers 102 on a shell-side surface 100b. The moisture wicking fibers are preferably hydrophilic nylon fibers such as "Hydrofil," but may include other hydrophobic fibers such as polypropylene or "Coolmax" polyester. The hydrophilic fibers 101 may consist of cotton, hydrophilic nylon, rayon, wool, blends of these fibers, or other similar hydrophilic fibers. In an alternate embodiment, the moisture transport insert 81 is constructed of a single-layer fabric formed substantially of hydrophobic polyester fibers, such as "Coolmax", having a high surface area in relation to volume.

According to yet another embodiment (not shown), the moisture wicking overlay and/or the moisture transport insert may be formed of an integrally knit tri-component fabric. This fabric is constructed of hydrophobic polyester fibers on an innermost skin side surface, a first hydrophilic nylon component residing adjacent to the hydrophobic polyester fibers, and a second hydrophilic nylon component residing adjacent to the first hydrophilic nylon fabric and comprising an outermost shell-side surface of the tri-component fabric. Preferably, the second hydrophilic nylon fabric has a brushed outer surface for enhancing the ability of the second nylon fabric to disperse moisture moved outwardly from the first nylon fabric. The hydrophilic nylon may be the "Hydrofil" fibers manufactured by Allied Fibers Corporation, or "Intera" nylon.

In either embodiment of the suspended panel of the garments described above, additional fabric layers may be added to the suspended panel to handle larger quantities of moisture and to increase the moisture absorption and dispersal characteristics of the panel. The additional fabric layers may include polyester or cotton fibers, or a combination of polyester and cotton fibers. Furthermore, the inner fabric layer of the suspended panel may have a longitudinally-extending opening or slit through which the added fabric layers may be inserted into the panel. The added fabric layers may be launderable and reusable, or disposable.

A launderable and reusable garment incorporating a moisture management suspended panel according to the present invention is described above. Various details of the invention may be changed without departing from its scope. Furthermore, the foregoing description of the preferred embodiment of the invention is provided for the purpose of illustration only and not for the purpose of limitation—the invention being defined by the claims.

We claim:

1. A garment constructed of an outer shell fabric and having an inner moisture management suspended panel located adjacent to the outer shell fabric and attached at one end thereof to a front waist area of the garment and attached at a second end thereof to a back seat area of the garment for preventing the movement of moisture from the body of the wearer to the outer shell fabric of the garment.

2. A garment having a inner moisture management suspended panel attached at one end thereof to a front waist area of the garment, and attached at a second end thereof to a back seat area of the garment, the suspended panel comprising:
  (a) an inner fabric layer constructed of moisture wicking fibers for residing in skin contact during garment wear;
  (b) an intermediate fabric layer residing adjacent to said inner fabric layer and formed of one or more fabrics for receiving and dispersing moisture wicked outwardly by said inner fabric layer; and
  (c) an outer fabric layer comprising a liquid impermeable, vapor permeable shield for providing a leakproof barrier which prevents passage of liquid but permits dissipation of moisture in vapor form through the fabric, said shield residing adjacent to said intermediate fabric layer and comprising the outermost fabric layer of said suspended panel.

3. A garment according to claim 2, wherein said intermediate fabric layer of the suspended panel comprises a moisture transport insert having a lower first portion and an upper second portion, said lower first portion residing generally adjacent a lower crotch area of the garment and being relatively narrow with a relatively small surface area; and the upper second portion of said moisture transport insert residing generally adjacent an upper crotch area of the garment and being relatively wide with a relatively large surface area, said second portion for providing greater moisture absorption capacity in the upper crotch area to promote the transport of moisture upwardly towards a drier area of the suspended panel where moisture can be more easily dispersed.

4. A garment according to claim 3, wherein the width of said moisture transport insert tapers from the relatively wide second portion towards the relatively narrow first portion.

5. A garment according to claim 2, wherein said intermediate fabric layer of the suspended panel comprises:
(a) a first fabric comprising a moisture wicking overlay carried by the suspended panel for moving moisture away from the skin, and having a skin-side surface and a shell-side surface, said moisture wicking overlay defining an opening therethrough from said skin-side surface to said shell-side surface; and
(b) a second fabric comprising a moisture transport insert extending through the opening in said moisture wicking overlay, and having:
(1) a lower first portion positioned in overlying relation on the skin-side surface of the moisture wicking overlay for receiving moisture from the skin and from the moisture wicking overlay; and
(2) an upper second portion positioned in overlying relation on the shell-side surface of said moisture wicking overlay for receiving moisture from the first portion of the moisture transport insert and for transporting the moisture through the opening to the shell-side surface of the moisture wicking overlay for dispersal throughout the shell-side surface.

6. A garment according to claim 5, wherein said moisture wicking overlay defines a second opening therethrough located in spaced-apart relation to said first opening for receiving a free end of the first portion of said moisture transport insert through said moisture wicking overlay from the skin-side surface of said moisture wicking overlay to the shell-side surface of said moisture wicking overlay.

7. A garment according to claim 6, wherein said moisture wicking overlay comprises a fabric constructed substantially of moisture wicking fibers having a high surface area in relation to their volume.

8. A garment according to claim 5, wherein said moisture wicking overlay comprises an integrally knit bi-component fabric constructed of moisture wicking fibers on the skin-side surface thereof for residing nearest the skin of the wearer, and hydrophilic fibers on the shell-side surface thereof for residing away from the skin of the wearer.

9. A garment according to claim 3 or 5, wherein said moisture transport insert comprises a fabric constructed substantially of moisture wicking fibers having a high surface area in relation to volume.

10. A garment according to claim 3 or 5, wherein said moisture transport insert comprises hydrophilic nylon fibers chemically processed for speeding the movement of moisture along the shaft of the fibers.

11. A garment according to claim 3 or 5, wherein said moisture transport insert comprises an integrally knit bi-component fabric constructed of moisture wicking fibers on the skin-side surface thereof for residing nearest the skin of the wearer, and hydrophilic fibers on the shell-side surface thereof for residing away from the skin of the wearer.

12. A garment according to claim 11, wherein the moisture wicking fibers of said bi-component moisture transport insert comprise hydrophilic nylon fibers.

13. A garment according to claim 11, wherein the hydrophilic fibers of said bi-component moisture transport insert comprise cotton fibers for absorbing and dispersing moisture wicked outwardly by said moisture wicking fibers.

14. A garment according to claim 2, wherein said inner fabric layer is constructed substantially of moisture wicking fibers having a high surface area in relation to volume.

15. A garment according to claim 2 wherein said inner fabric layer comprises an integrally knit bi-component fabric constructed of moisture wicking fibers on a skin-side surface thereof for residing nearest the skin of the wearer, and hydrophilic fibers on an shell-side surface thereof for residing away from the skin of the wearer.

16. A garment according to claim 15, wherein the moisture wicking fibers of the bi-component inner fabric layer comprise hydrophobic polyester fibers.

17. A garment according to claim 16, wherein the hydrophilic fibers of the bi-component inner fabric layer comprise hydrophilic nylon fibers.

18. A garment according to claim 2, wherein said inner fabric layer comprises an integrally knit tri-component fabric constructed of moisture wicking fibers on a skin-side surface thereof for residing nearest the skin of the wearer, a first hydrophilic fiber component residing adjacent to said moisture wicking fibers, and a second hydrophilic fiber component residing adjacent to said first hydrophilic fiber component and comprising the shell-side surface of said tri-component fabric.

19. A garment according to claim 18, wherein the surface of said second hydrophilic fiber component adjacent to said first hydrophilic fiber component is brushed for enhancing the ability of the second hydrophilic component to disperse moisture moved outwardly from the first hydrophilic component.

20. A garment according to claim 2, wherein the first and second ends of the suspended panel include first and second elastic end segments for being attached respectively to the front waist area of the garment and to the back seat area of the garment, each of said elastic end segments being constructed of elastic yarns to provide stretchability for allowing the suspended panel to reside closely and comfortably next to the skin of the wearer.

* * * * *